(12) United States Patent
Nichols et al.

(10) Patent No.: US 7,560,071 B2
(45) Date of Patent: Jul. 14, 2009

(54) INSTRUMENT DOCKING STATION FOR AN AUTOMATED TESTING SYSTEM

(76) Inventors: Michael J. Nichols, 99 Farquhar St., #3, Roslindale, MA (US) 02131; Louis J. Guarracina, 19 Canterbury Hill Rd., Topsfield, MA (US) 01983

( * ) Notice: Subject to any disclaimer, the term of this patent is extended or adjusted under 35 U.S.C. 154(b) by 51 days.

(21) Appl. No.: 11/394,373

(22) Filed: Mar. 29, 2006

(65) Prior Publication Data
US 2007/0237675 A1    Oct. 11, 2007

(51) Int. Cl.
*G01N 35/00* (2006.01)
(52) U.S. Cl. .................. 422/63; 422/65; 422/68.1; 436/43; 436/45; 436/47; 414/663; 414/222.01
(58) Field of Classification Search .............. 422/63, 422/65, 68.1; 436/43, 45, 47; 414/663, 222.01
See application file for complete search history.

(56) References Cited

U.S. PATENT DOCUMENTS

| | | | | |
|---|---|---|---|---|
| 4,537,552 A | * | 8/1985 | Slee | 414/226.04 |
| 4,965,049 A | * | 10/1990 | Lillig et al. | 422/68.1 |
| 5,207,986 A | * | 5/1993 | Kadota et al. | 422/65 |
| 5,746,976 A | * | 5/1998 | Yamada et al. | 422/62 |
| 5,928,952 A | * | 7/1999 | Hutchins et al. | 436/50 |
| 6,019,945 A | * | 2/2000 | Ohishi et al. | 422/65 |
| 6,060,022 A | * | 5/2000 | Pang et al. | 422/65 |
| 6,132,685 A | * | 10/2000 | Kercso et al. | 422/104 |
| 6,290,907 B1 | * | 9/2001 | Takahashi et al. | 422/65 |
| 6,337,050 B1 | * | 1/2002 | Takahashi et al. | 422/65 |
| 6,447,236 B1 | * | 9/2002 | Grams et al. | 414/401 |
| 6,524,057 B1 | * | 2/2003 | Park | 414/663 |
| 6,764,650 B2 | * | 7/2004 | Takahashi et al. | 422/65 |
| 6,780,064 B2 | * | 8/2004 | Abel et al. | 439/717 |
| 2001/0043882 A1 | * | 11/2001 | Berger et al. | 422/67 |
| 2003/0215357 A1 | * | 11/2003 | Malterer et al. | 422/50 |

* cited by examiner

*Primary Examiner*—Jill Warden
*Assistant Examiner*—P. Kathryn Wright
(74) *Attorney, Agent, or Firm*—Hoffman Warnick LLC

(57) ABSTRACT

An automated testing system includes one or more laboratory devices that operate together to perform an assay. The testing system is designed such that a laboratory device may be seamlessly integrated with the remaining devices in a quick and effortless manner. Specifically, the laboratory device is securely mounted on a slidable cart with fluid and electrical connections established therebetween. The slidable cart is in turn adapted to releasably engage with a docking station that is fixedly mounted on the workspace floor, the docking station being provided with at least one fluid input connection, an input power connection and at least one communication signal connection that are relatively permanent in nature. In order to couple the cart to the docking station, the cart is rolled generally into position above the docking station using complementary alignment posts and tracks.

12 Claims, 19 Drawing Sheets

INSTRUMENT DOCKING STATION FOR AN AUTOMATED TESTING SYSTEM

BACKGROUND OF THE INVENTION

The present invention relates generally to the life sciences industry and more particularly to automated testing systems for conducting high throughput screening in the life sciences industry.

High throughput screening (HTS) is a well-known form of scientific experimentation in the life sciences industry which enables a research facility to conduct a large quantity of experiments at the same time. Specifically, in one form of high throughput screening which is well-known in the art, a plate is provided which includes a large number of isolated, miniaturized wells (e.g., 96, 384 or 1536 wells per plate), whereby a unique compound is disposed within each well. An array of different substances is then deposited into each well with the premise of discovering a desired reaction. In this manner, high throughput screening can be used to subject a particular substance to an entire library of compounds at the same time and, as a result, is highly useful in the discovery of new medicines, vaccines and biopharmaceuticals.

High throughput screening is often performed in an environmentally-controllable enclosure which is commonly referred to as a cell or chamber. As can be appreciated, a laboratory cell affords researchers with an enclosed environment that is most suitable for testing, which is highly desirable.

High throughput screening also traditionally relies on automation to conduct assays which are otherwise repetitive in nature, provided that the close control and intricate manipulative skills of human operators can be faithfully replicated using conventional robotics (e.g., multi-axis robots). Various types of laboratory automation tools are presently used in conjunction with high throughput screening. Examples of well-known laboratory automation tools range from simple semi-automated liquid handling devices to fully integrated automated systems that comprise, among other things, multiple robot arms, integrated lamp devices, pipetting stations, centrifuges, incubators, plate washers, and detectors.

It has been found that the use of automation in conjunction with high throughput screening (as well as other forms of experimentation in the life sciences industry) provides two principal advantages.

As a first advantage, automation significantly reduces the degree of human involvement required to conduct this form of experimentation, thereby providing research facilities with considerable advantages in both safety and overall laboratory costs, which is highly desirable.

As a second advantage, automation significantly improves the overall speed of testing. As a consequence, automation enables a greater number of assays to be performed in a shorter period of time, which is highly desirable.

It should be noted that certain automated laboratory devices that are used in conjunction with conducting experiments in the life sciences industry are typically fixedly mounted (e.g., bolted) either onto a common cell table or onto the workstation floor. As can be appreciated, each laboratory device must be locked in place to ensure that the device seamlessly integrates with the other laboratory devices at a high level of repeatability. With the laboratory device fixed in place, all of the necessary fluid and/electrical inputs are the supplied to the laboratory device by a laboratory technician for use in its operation.

As can be appreciated, the applicant has discovered that the above-described method of integrating an automated laboratory device into an automated testing system introduces at least some of the following shortcomings.

As a first shortcoming, the above-described method of permanently securing an automated laboratory device to a particular surface greatly inhibits both (i) the future integration of additional laboratory devices and (ii) the repair and/or upgrading of the laboratory device. As a consequence, it has been found that the effective life of the automated system is minimized, which is highly undesirable.

As a second shortcoming, the above-described method of performing numerous, individualized, manual input connections into each automated laboratory device renders the entire installation process (i.e., system set-up) time-consuming, cumbersome and complex in nature, which is highly undesirable.

As a third shortcoming, the above-described method of permanently securing an automated laboratory device to a particular surface renders the device unavailable for use in conjunction with alternate testing throughout the lifespan of the system. Because certain laboratory devices are expensive to purchase, the inability to use a single laboratory device in conjunction with multiple simultaneous experiments substantially increases the costs incurred at a life science research facility, which is highly undesirable.

SUMMARY OF THE INVENTION

It is an object of the present invention to provide a new and improved system for use in conducting testing in the life sciences industry.

It is another object of the present invention to provide a system of the type as described above that includes at least one automated laboratory device.

It is yet another object of the present invention to provide a system of the type as described above wherein the automated laboratory device can be integrated into the system with a high level of repeatability.

It is still another object of the present invention to provide a system of the type as described above wherein the automated laboratory device can be integrated into the system in a quick and effortless manner.

It is yet still another object of the present invention to provide a system of the type as described above which is simple in its construction and which is inexpensive to manufacture.

Accordingly, there is provided a system for use in conducting an assay, said system comprising (a) a laboratory device for performing a particular function in conjunction with the assay, (b) a movable cart sized and shaped to support the laboratory device, and (c) a fixedly mounted docking station that is designed to releasably engage with the movable cart, (d) wherein, with the cart engaged with the docking station, at least one of fluid and electrical connection is established between the cart and the docking station.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration particular embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate an embodiment of the invention and, together with the description, serve to explain the principles of the invention. In the drawings wherein like reference numerals represent like parts.

DETAILED DESCRIPTION OF A PREFERRED EMBODIMENT

Figure 1:
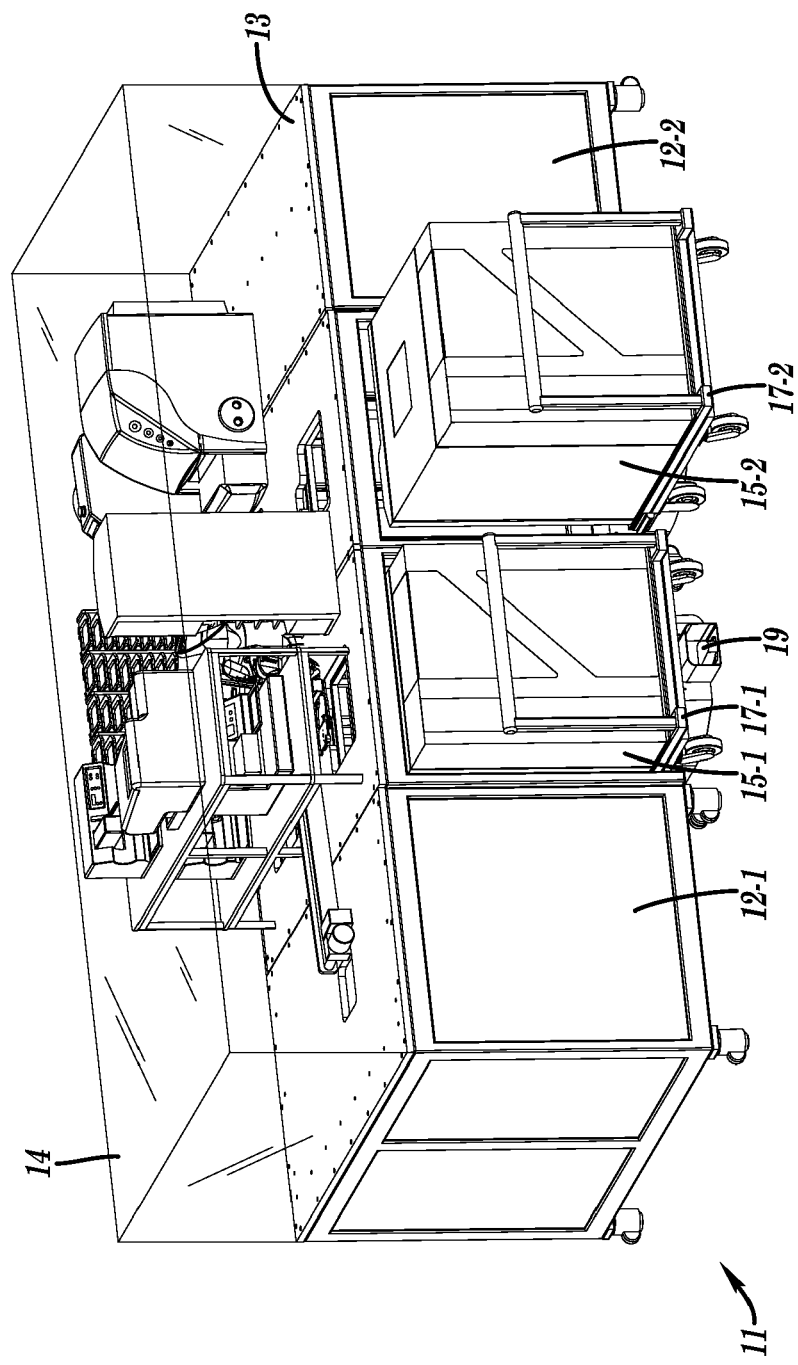
FIG. 1 is a top perspective view of an automated testing system constructed according to the teachings of the present invention.

Referring now to FIG. 1, there is shown an automated testing system that is constructed according to the teachings of the present invention, said automated testing system being identified generally by reference numeral 11. As can be appreciated, system 11 is designed principally for use in conducting laboratory research in the life sciences industry and may be used, more specifically, to perform high throughput screening (HTS) in the life sciences industry.

Automated Testing System (11)

System 11 comprises a pair of fixedly mounted end units 12-1 and 12-2 which together support a flat table surface 13 on which certain laboratory devices are fixedly mounted. Preferably, a transparent testing chamber 14 is mounted on table surface 13 over said devices in order to provide an enclosed testing environment that may be regulated by the operator to optimize results.

System 11 additionally includes a pair of automated laboratory devices 15-1 and 15-2 that are configured to be readily integrated into the above-described testing environment. It should be noted that each laboratory device 15 represents any well-known piece of laboratory equipment which is commonly used in conjunction with laboratory testing in the life sciences industry, device 15 preferably being either semi-automatic or fully-automatic in nature. For example, laboratory device 15 may represent, inter alia, a multi-axis robot, an integrated lamp device, a pipetting station, a centrifuge, an incubator, a plate washer, a detector, a plate carousel or some combination thereof.

Figure 2A:
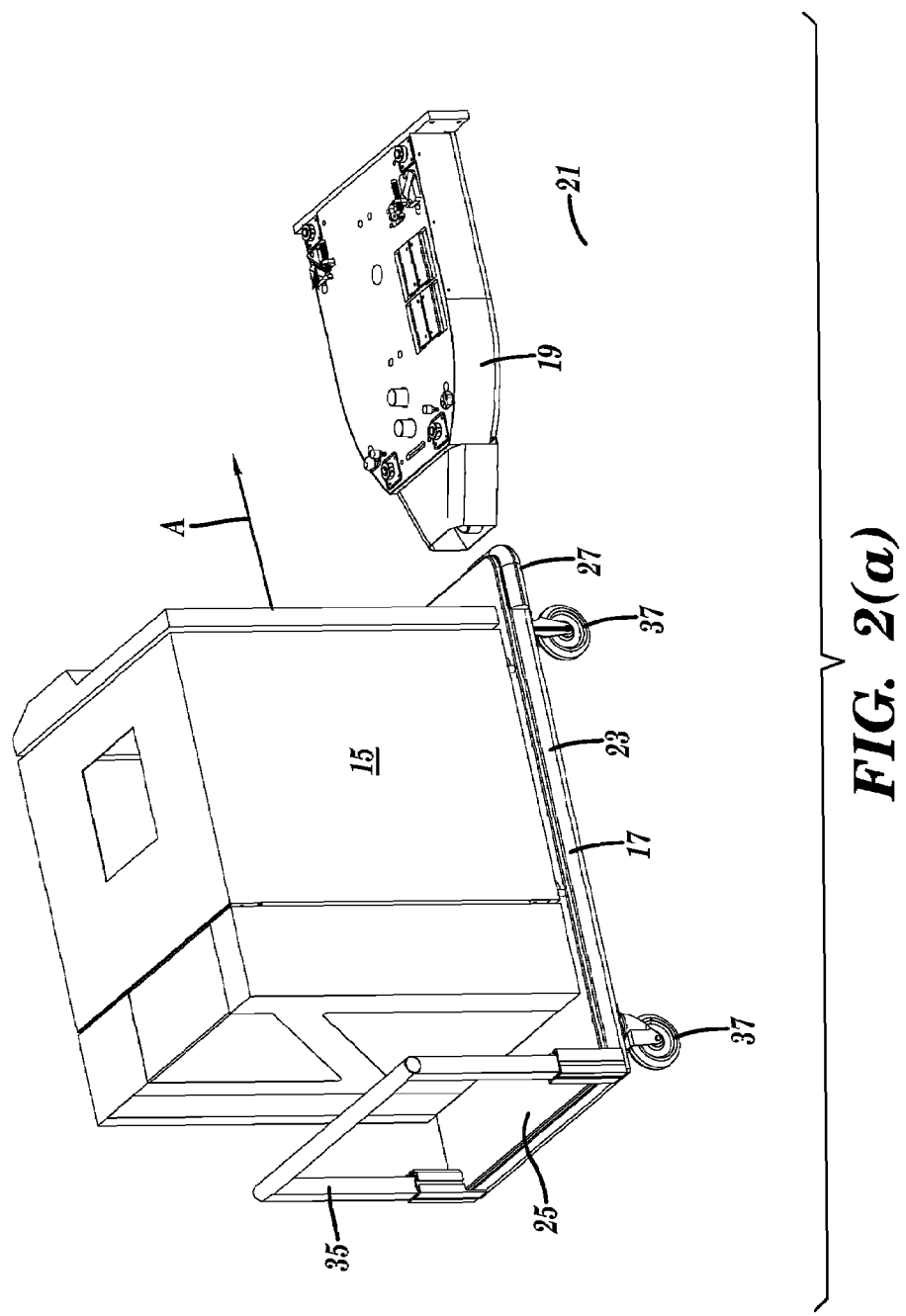
FIG. 2(a) is a top perspective view of one of the laboratory devices shown in FIG. 1, the laboratory device being shown mounted on a cart that is disengaged from a docking station.
Figure 2B:
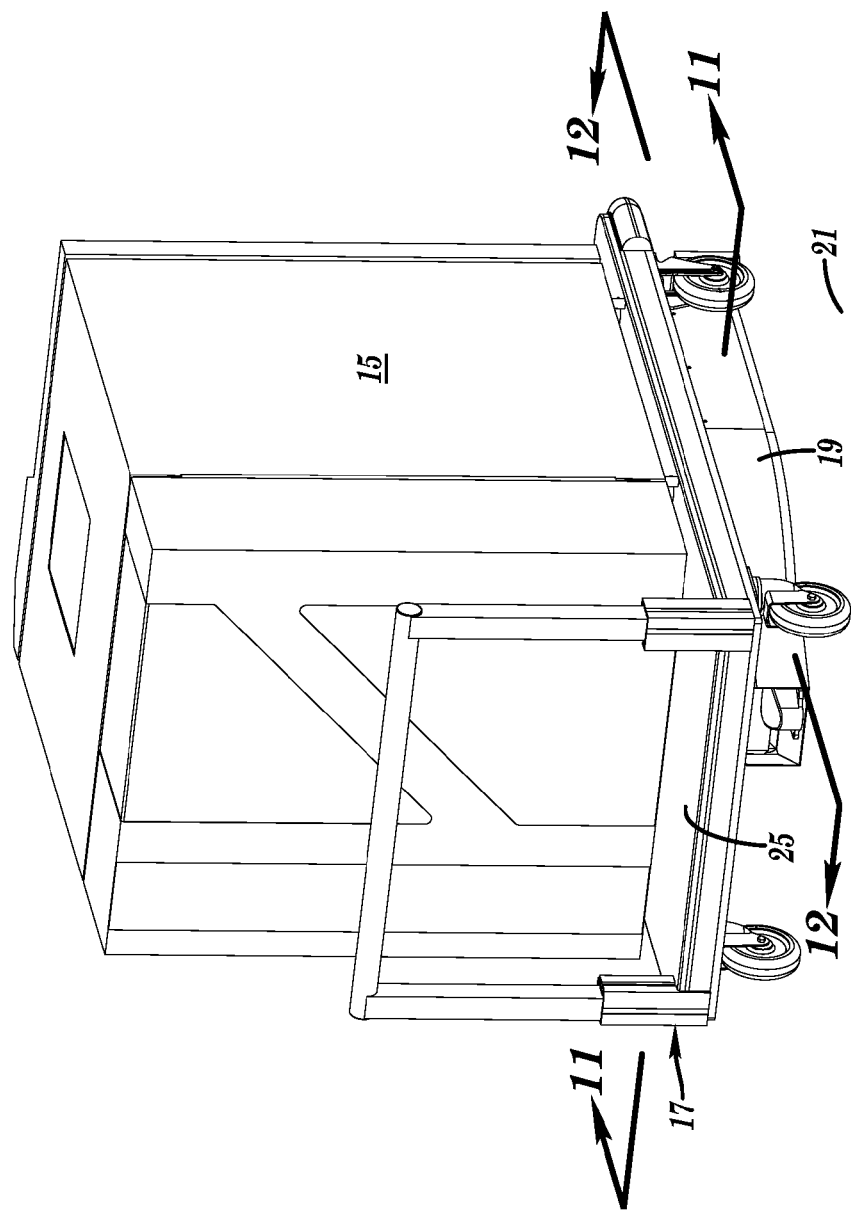
FIG. 2(b) is a side perspective view of one of the laboratory devices shown in FIG. 1, the laboratory device being shown mounted on a cart that is engaged with a docking station.

Laboratory devices 15-1 and 15-2 are shown fixedly mounted on corresponding carts 17-1 and 17-2, respectively. As shown in FIGS. 2(a) and 2(b), each cart 17 is designed to releasably engage with an associated docking station 19 that is, in turn, fixedly mounted onto workspace floor 21. As will be described in detail below, the particular interrelationship between carts 17 and docking stations 19 facilitates both (i) the seamless integration of devices 15 into system 11 and (ii) the withdrawal of any device 15 from system 11 (e.g., to allow for the repair, upgrading and/or alternate use of said device) and therefore serves as a principal novel feature of the present invention.

It should be noted that system 11 is not limited to use of any particular type and/or number of individual laboratory devices 15. Rather, it is to be understood that the type and/or number of laboratory devices 15 that are used in system 11 may vary depending on the particular type of testing to be performed.

System 11 further includes a central computer system (not shown) that is preferably mounted in a rack that is integrally provided in one of the fixed end units 12. With the central computer system located as such, the overall footprint (i.e., dimensions) for system 11 is rendered more compact in nature, which is a necessity in most laboratory settings in the life sciences industry.

The central computer system is electronically linked with each of the various laboratory devices 15 by means of a standard communication network, as will be described further below. It should be noted that each device 15 may connect directly to a communication port for the computer system or, in the alternative, to a common network hub which is in turn connected to the computer system (e.g., via ethernet communication means). In use, the central computer system serves to, among other things, (i) control the operation of the various devices 15 (i.e., manage the automated testing process within chamber 14) and (ii) compile the data that results from said testing (either using an internal database or by linking with an external database).

Cart (17)

As noted above, each cart 17 is designed to support an associated laboratory device 15. Preferably, each cart 17 is modular and universal in its construction and is thereby capable of supporting a wide range of different laboratory devices 15.

Figure 3:
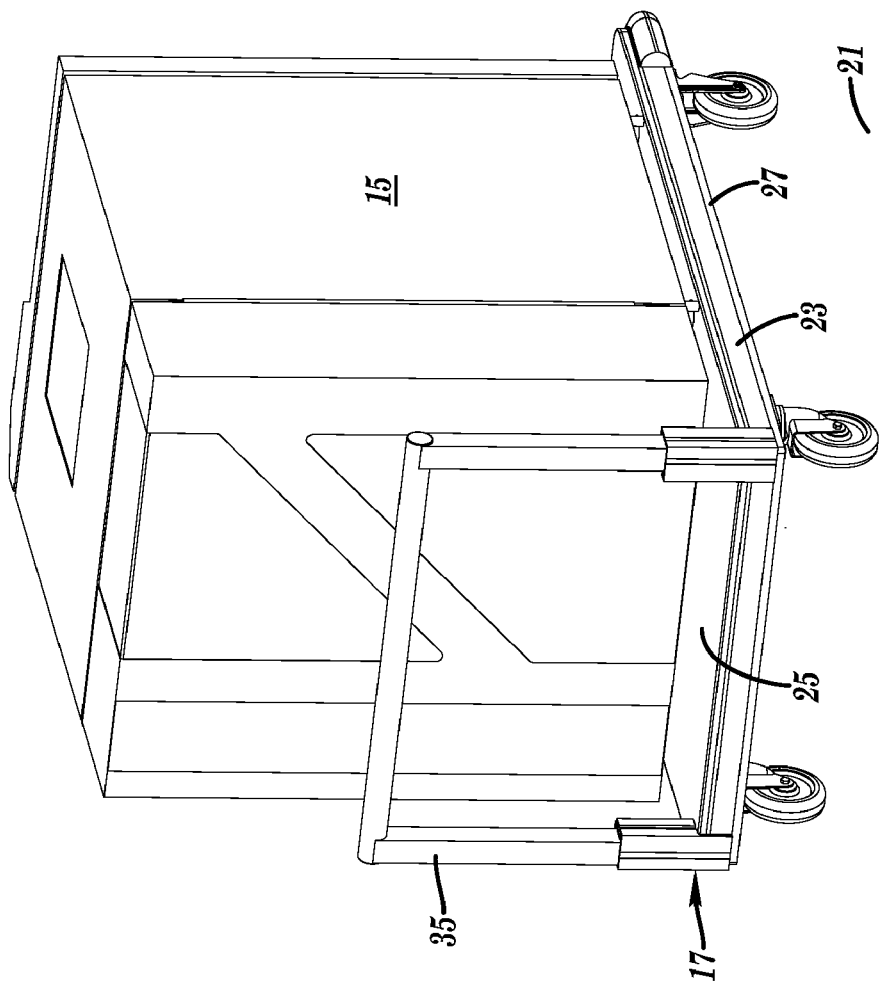
FIG. 3 is a top perspective view of the laboratory device and cart shown in FIG. 2(a)
Figure 4:
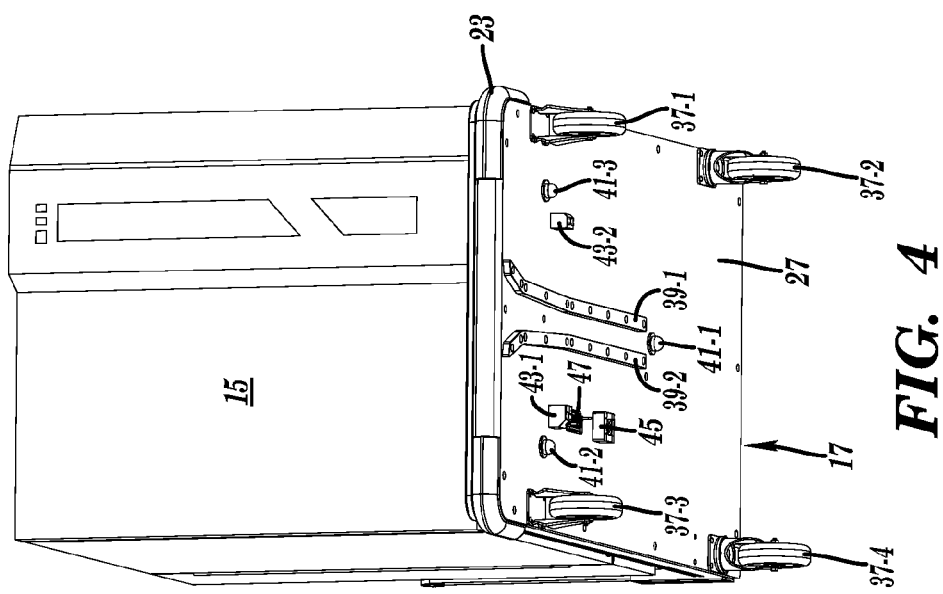
FIG. 4 is bottom perspective views of the laboratory device and cart shown in FIG. 2(a)

Referring now to FIGS. 3 and 4, each cart 17 comprises a substantially square-shaped frame 23. A substantially flat top panel 25 is mounted to the top of frame 23 and is secured in place relative thereto using conventional fastening elements (e.g., screws). Similarly, a substantially flat bottom panel 27 is mounted to the underside of frame 23 and is secured in place relative thereto using conventional fastening elements (e.g., screws). As seen in the drawings, frame 23 and top panel 25 together support the laboratory device 15 that is mounted on cart 17 and, as a result, are preferably constructed out of a rigid, strong and durable material, such as metal.

As seen most clearly in FIG. 3, each cart 17 preferably includes a generally U-shaped handle 35 which extends upward from the rear edge of frame 23. As will be described further below, handle 35 facilitates in the manual manipulation of cart 17.

Preferably, each laboratory device 15 is fixedly mounted on top panel 25 of its corresponding cart 17 using any well-known alignment/retention means (e.g., complementary pins and holes) in order to establish repeatability of position therebetween. In this manner, the alignment/retention means ensures that the device 15 will seamlessly integrate with the remainder of testing system 11, which is a principal object of the present invention.

As seen most clearly in FIG. 4, each cart 17 includes a plurality of wheels 37-1, 37-2, 37-3 and 37-4, a symmetrical pair of tracks 39-1 and 39-2, a plurality of alignment pins 41-1, 41-2 and 41-3, a pair of dampening blocks 43-1 and 43-2, a fluid connector 45 and an electrical connector 47, the particulars for each component to be described in detail below.

Wheels 37 are fixedly mounted onto bottom panel 27 using conventional fastening means (e.g., screws, bolts, etc.), with one wheel 37 positioned in each corner. Together, wheels 37 enable cart 17 to glide easily along a flat surface, such as workspace floor 21. In this manner, cart 17 facilitates moving laboratory device 15 in relation to the remainder of testing system 11.

Figure 5:
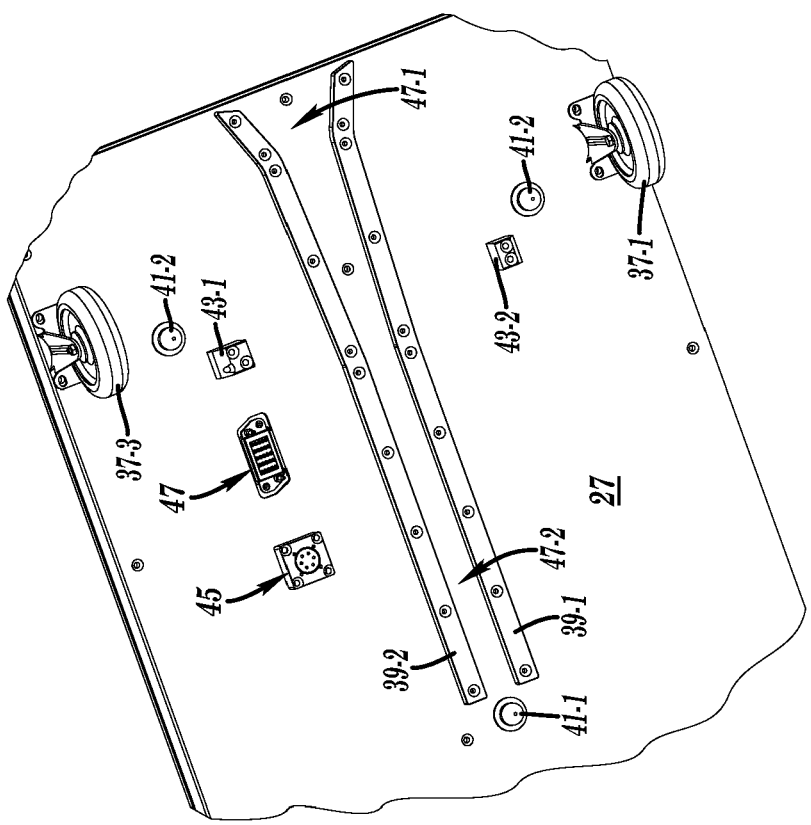
FIG. 5 is an enlarged, fragmentary bottom perspective view of the cart shown in FIG. 4.

Referring now to FIG. 5, tracks 39 are fixedly mounted to bottom panel 27 using any conventional fastening means (e.g., screws). As can be seen, tracks 39 are spaced apart from one another so as to define a post receiving channel 47 therebetween that is widened at its front end 47-1 and substantially narrowed towards its back end 47-2. As will be described further in detail below, tracks 39 serve as guide rails that facilitate in the proper positioning of cart 17 in relation to a corresponding docking station 19.

Alignment pins 41 are fixedly mounted to bottom panel 27 in a generally triangular configuration. As seen most clearly in FIG. 5, each alignment pin 41 has a hemispherical, or dome-like, shape. As will be described further in detail below, alignment pins 41 serve both (i) as a means for accurately aligning cart 17 in its proper position relative to docking station 19 (which is in turn used to position device 15 within chamber 13 with a high level or repeatability) and (ii) as the primary points of contact when docking station 19 lifts cart 17 upward off workspace floor 21.

Dampening blocks 43 are fixedly mounted to bottom panel 27 along its front edge. As will be described further below, dampening blocks 43 are used to decelerate cart 17 as it is rolled into position above a corresponding docking station 19.

Figure 6:
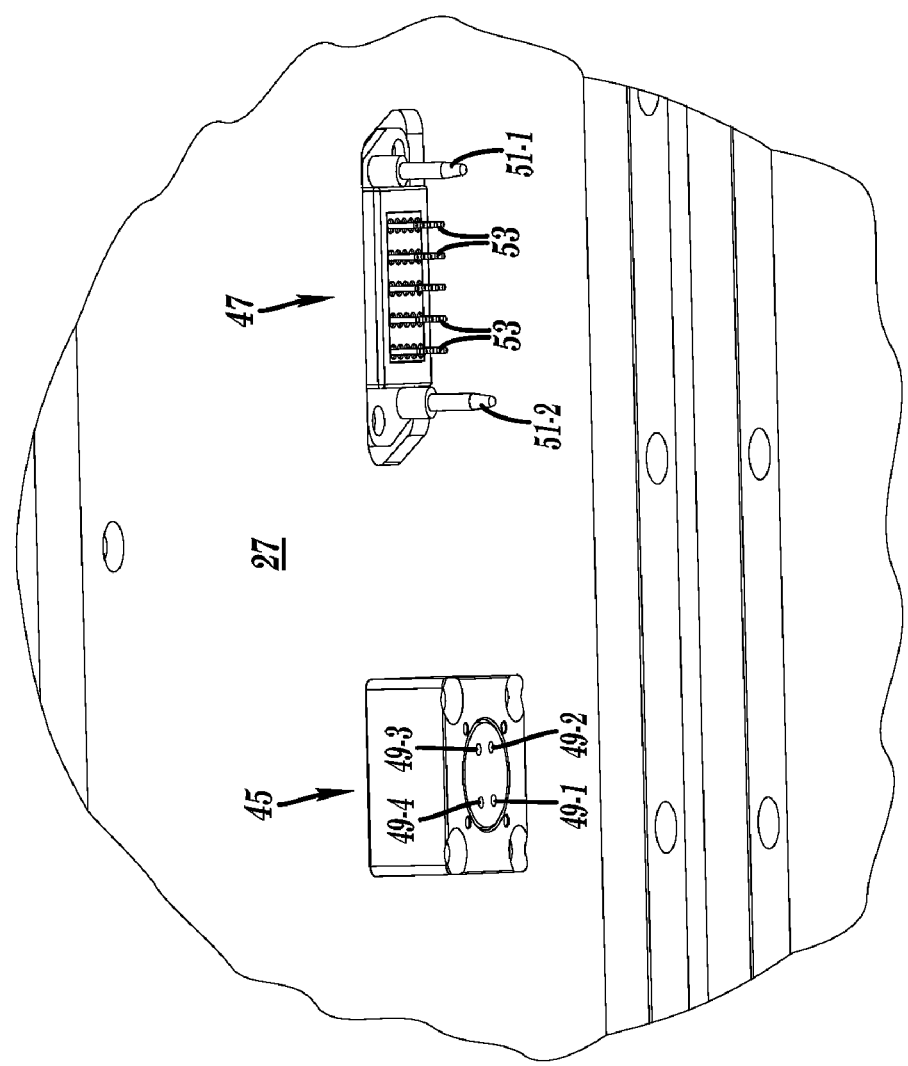
FIG. 6 is an enlarged, fragmentary bottom perspective view of the cart shown in FIG. 5.

Fluid connector 45 is fixedly mounted to bottom panel 27 and is fluidly connected with the particular laboratory device 15 that is mounted on cart 17. As seen most clearly in FIG. 6, fluid connector 45 comprises a plurality of isolated input fluid ports 49-1, 49-2, 49-3 and 49-4, wherein each input fluid port 49 is designated to deliver a particular fluid (e.g., compressed air, water, etc.) into an appropriate port in laboratory device 15. As defined herein, use of the term "fluids" is meant to denote liquids and/or gases.

As will be described in greater detail below, fluid connector 45 is adapted to matingly engage with a complementary fluid connector on docking station 19. In this manner, fluids are delivered to laboratory device 15 via cart 17 and docking station 19.

It should be noted that fluid connector 45 is not limited to a particular number of input fluid ports 49. Rather, it is to be understood that the number of input fluid ports 49 could be modified without departing from the spirit of the present invention.

Electrical connector 47 is fixedly mounted to bottom panel is electrically connected with the primary system electronics for laboratory device 15. As seen most clearly in FIG. 6, connector 47 is represented herein as being in the form of a male serial connector that includes a pair of power pins 51-1 and 5-2 and a plurality of individual electrical pins 53 which can be used, among other things, to transmit communication signals and to regulate the state of internal fluid valves, as will be described in greater detail below.

Preferably, selected pins 53 of electrical connector 47 are electrically connected to a microprocessor (not shown) that is embedded with cart 17 and that is programmed with a unique identification code for self-identification purposes. For example, the self-identification microprocessor may be of the type that is manufactured and sold by Maxim Integrated Products, Inc. of Sunnyvale, Calif. under the name iButton®. As can be appreciated, the provision of a self-identifying microprocessor in cart 17 enables the central computer system to immediately identify each laboratory device 15 that is installed into testing system 11, which is highly desirable.

It is to be understood that cart 17 may be provided with alternative means of self-identification without departing from the spirit of the present invention. For example, each cart 17 may include an ethernet device with a unique IP address which can be used for identification purposes.

Docking Station (19)

As noted briefly above, docking stations 19 are designed to releasably engage with carts 17. More specifically, it is to be understood that each docking station 19 serves two principal functions: (i) to mechanically lift cart 17 off the workspace floor 21 so that the laboratory device 15 mounted thereon is integrated into testing system 11 with a high degree of repeatability and (ii) to provide a quick, automated means of delivering the requisite electrical and fluid inputs to cart 17 which are, in turn, delivered the laboratory device 15 mounted thereon.

Figure 7A:
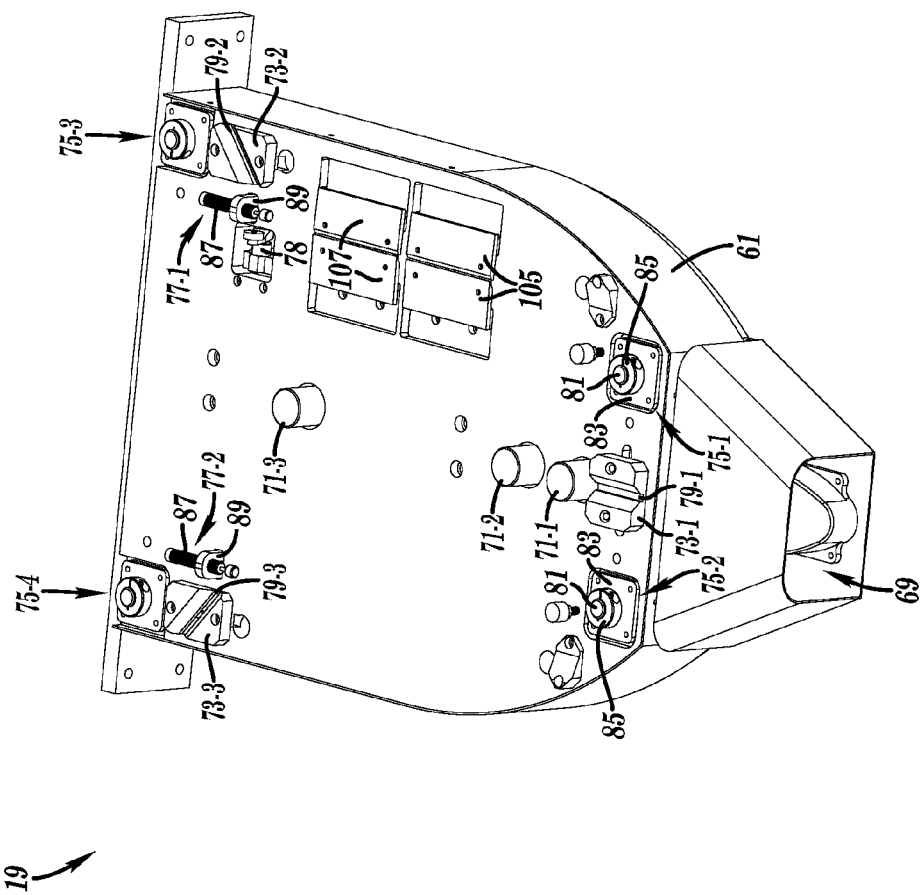
FIGS. 7(a) and (b) are enlarged, top perspective views of the docking station shown in FIG. 2(a) at various stages during the displacement of its top plate relative to its base.
Figure 7B:
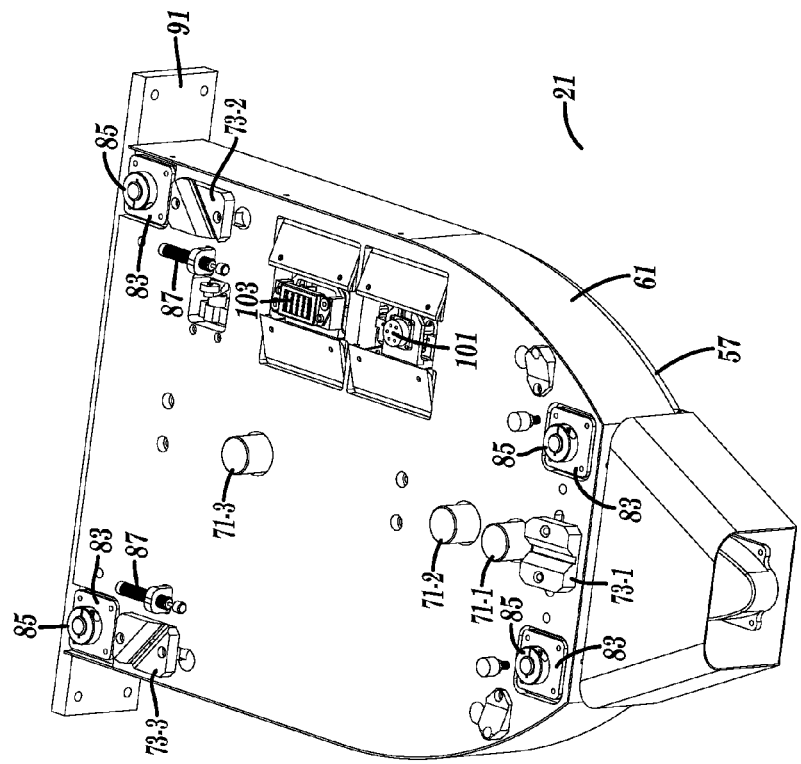
Figure 8:
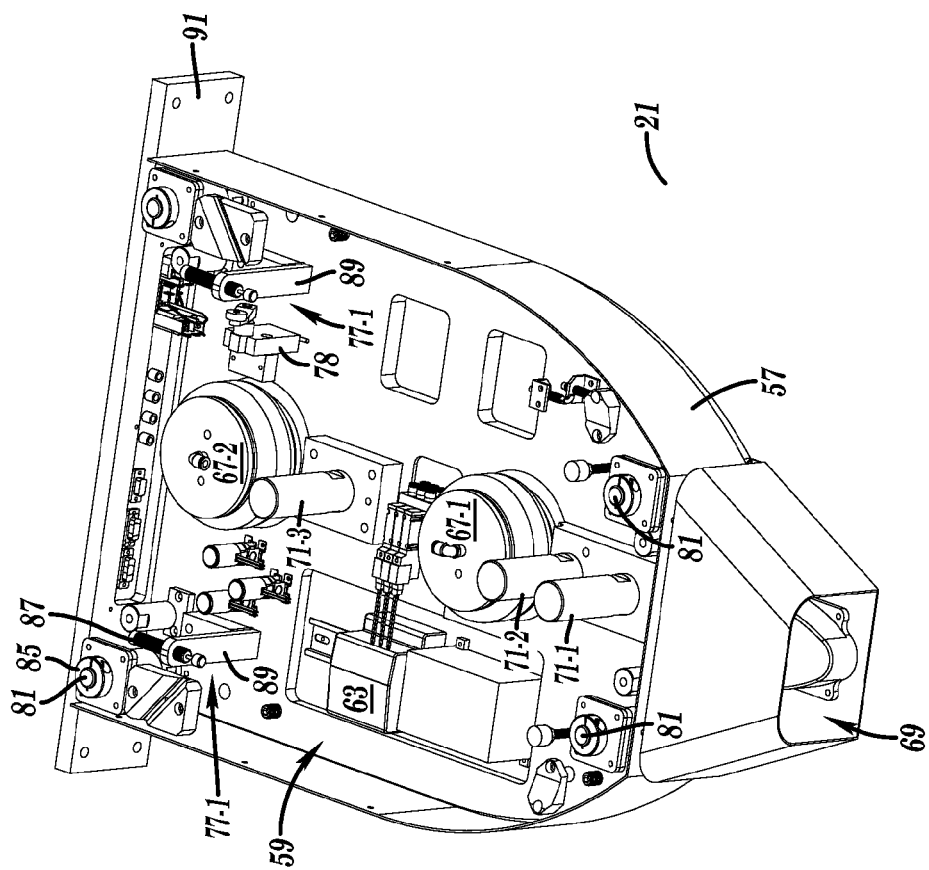
FIG. 8 is a top perspective view of the docking station shown in FIG. 7(a), the docking station being shown with its top plate removed therefrom.

Referring now to FIGS. 7(a), 7(b) and 8, each docking station 19 is constructed to include a base 57 that is fixedly mounted in place on workstation floor 21 (e.g., using bolts, screws, etc.). Base 57 is centrally recessed so as to define an interior cavity 59 that is sized and shaped to retain the majority of the electrical components for docking station 19. A top plate 61 is slidably mounted over base 57 so as to substantially enclose interior cavity 59. Preferably, base 57 and top plate 61 are both constructed out of a rigid, strong and durable material, such as steel or aluminum, for reasons to become apparent below.

A programmable logic controller (PLC) 63 is preferably disposed within interior cavity 59 and is responsible for managing the principal operations of docking station 19.

A pair of inflatable bladders 67-1 and 67-2 is also preferably disposed within interior cavity 59. When inflated with compressed air, bladders 67 displace top plate 61 upward and away from base 57, as seen most clearly in FIGS. 7(a)-7(b). As will be described further in detail below, the upward displacement of top plate 61 serves to both (i) lift cart 17 off workspace floor 21 and (ii) establish fluid and electrical connection between cart 17 and docking station 19.

Bladders 67 are designed for actuation through the depression of a foot pedal 69. Specifically, the depression of foot pedal 69 generates an electrical signal that is received by PLC 63. If PLC 63 determines that a cart 17 is properly positioned above the docking station 19, PLC 63 activates the inflation of bladders 67.

It should be noted that docking station 19 is not limited to the use of pneumatic means for raising top plate 61 relative to base 57. Rather, it is to be understood that alternative means for raising top plate 61 relative to base 57 (e.g., conventional mechanical linkages) could be used in place of said pneumatic means without departing from the spirit of the present invention.

It should also be noted that docking station 19 is not limited to the implementation of a foot pedal 69 to actuate inflatable bladders 67. Rather, it is to be understood that alternative actuation means (e.g., a finger-activated electrical switch) could be implemented in place thereof without departing from the spirit of the present invention.

As seen most clearly in FIG. 7(a), docking station 19 additionally comprises a plurality of alignment posts 71-1, 71-2 and 71-3, a plurality of alignment blocks 73-1, 73-2 and 73-3, a plurality of top plate stop assemblies 75-1, 75-2, 75-3 and 75-4, a pair of shock absorbers 77-1 and 77-2, and a mechanical switch 78, the details of each component to be described in detail below.

Alignment posts 71 are arranged in a co-linear configuration, each alignment post 71 being generally cylindrical in shape and rigid in its construction. One end of each post 71 is fixedly coupled to the top surface of base 57 (e.g., by brackets), as seen most clearly in FIG. 8, with the opposite end of each post 71 extending orthogonally upward and through a corresponding circular opening in top plate 61, as seen most clearly in FIG. 7(a). In this manner, the free end of each post 71 protrudes slightly above top plate 61. As will be described further below, the exposed portions of posts 71 cooperate with tracks 39 to roughly guide cart 17 into its proper position above docking station 19 prior to actuation of foot pedal 69.

Alignment blocks 73 are fixedly mounted onto the top surface of top plate 61 in a triangular formation, as seen most clearly in FIGS. 7(a) and 7(b). Alignment blocks 73-1, 73-2 and 73-3 are shaped to include V-shaped grooves 79-1, 79-2 and 79-3, respectively, which in turn are sized and shaped to fittingly receive alignment pins 41-1, 41-2 and 41-3, respectively, on cart 17, as will be described further in detail below. It should be noted that the plurality of grooves 79 extend in different directions in order to provide two-dimensional accuracy of cart 17 relative to docking station 19.

Stop assemblies 75 are spaced adequately apart from one another and together serve to limit the degree that top plate 61 may be displaced upward and, as a result, the height that cart 17 may be lifted off workspace floor 21. As seen most clearly in FIG. 8, each stop assembly 75 includes a cylindrical post 81 that is affixed at one end to the top surface of base 57 (e.g., by brackets). As seen most clearly in FIG. 7(a), the opposite end of each post 81 extends orthogonally upward and fittingly protrudes through a circular opening provided in a stop bearing 83 that is fixedly mounted on top plate 61. An enlarged annular stop 85 is fixedly mounted on the free end of each post 81 and is sized and shaped to abut against its associated bearing 83 once top plate 61 advances a pre-determined distance upward, as seen most clearly in FIG. 7(b).

Shock absorbers 77-1 and 77-2 are fixedly coupled to base 57 of docking station 19 in a spaced apart relationship, as seen most clearly in FIG. 8. Each shock absorber 77 includes a horizontally disposed, spring-biased damper 87 that is supported by a vertically-disposed mounting bracket 89 that fittingly protrudes through a corresponding slot formed in top plate 61. In this manner, each damper 87 is spaced slightly above the top surface of top plate 61 and extends substantially parallel relative thereto, as seen most clearly in FIGS. 7(a) and 7(b). As will be described further below, dampers 87 are used as cart 17 is being rolled into place above a corresponding docking station 19. Specifically, dampers 87 serve two principal functions: (i) to limit the degree of forward displacement of cart 17 relative to docking station 19 and (ii) to adequately decelerate cart 17 as it is being rolled into position, thereby absorbing the force of the cart 17 (as well as the laboratory device 15 mounted thereon) in order to minimize the risk of any physical damage to either the cart 17, device 15 or docking station 19 during the installation process.

Mechanical switch 78 is electrically connected to PLC 63 and at least partially protrudes out through an opening formed in top plate 61. Accordingly, as cart 17 is advanced into position above docking station 19, frame 23 of cart 17 actuates mechanical switch 78. The actuation of mechanical switch 78 produces an electrical signal that is received by PLC 63. In response thereto, PLC 63 supplies the power to bladders 67 that is required for their inflation upon activation of foot pedal 69.

Figure 9:
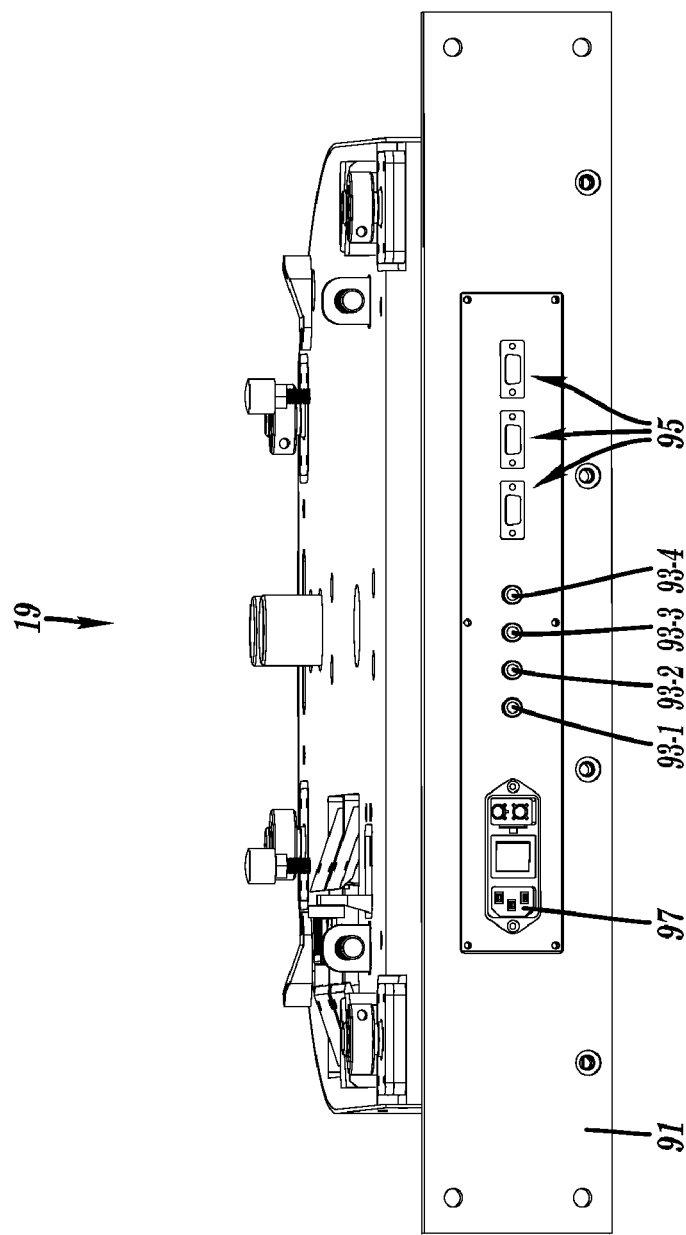
FIG. 9 is a front perspective view of the docking station shown in FIG. 7(a)

Each docking station 19 is designed to include, among other things, a power input, one or more serial communication outputs and one or more fluid inputs. Specifically, as seen most clearly in FIG. 9, an end plate 91 is fixedly mounted to base 57 and supports various fluid and electrical interfaces, as will be described in detail below.

Front plate 91 is represented herein as comprising four separate input fluid ports 93-1, 93-2, 93-3 and 93-4. Each port 93 is designated to receive a particular fluid (e.g., water, nitrogen, oxygen, compressed air, etc.) that is provided, for example, from a remote source.

Front plate 91 is represented herein as additionally comprising a plurality of communication signal connectors 95 which are electrically connected to PLC 63. Each connector 95 may be in the form of any conventional electrical connector that is designed principally for use in the transmission of communication data. For example, each communication signal connector 95 may be in the form of a standard serial port connector (e.g., a DB-9 serial port connector or an RJ-45 serial port connector). It should be noted that the establishment of a serial port connection between docking station 19 and the central computer system enables test results data to be passed therebetween, which is highly desirable.

Front plate 91 is represented herein as further comprising an input power connector 97 which is in turn electrically connected to PLC 63 for docking station 19. In this manner, it is to be understood that docking station 19 is supplied with the necessary power to operate.

It should be noted that the aforementioned fluid and electrical connections that are made with each docking station 19 are intended to be relatively permanent in nature. Because docking station 19 and cart 17 can be fluidly and electrically connected through the use of simple, automated means (as will be described in detail below), it is to be understood that the integration of an individual laboratory device 15 into testing system 11 eliminates the time-consuming process of individually connecting all of the assorted fluid and electrical inputs/outputs into the laboratory device 15.

As noted above, each docking station 19 is designed to fluidly and electrically connect with a corresponding cart 17 through the use of simple, automated means. Specifically, as seen most clearly in FIG. 7(b), each docking station 19 includes a fluid connector 101 and an electrical connector 103. As will be described further in detail below, fluid connector 101 is adapted to matingly engage with fluid connector 45 on cart 17 and electrical connector 103 is adapted to matingly engage with electrical connector 47 on cart 17. Through the use of these complementary pairs of mating connectors, fluid and electrical interconnection is established between docking station 19 and cart 17.

Referring now to FIGS. 7(a), 7(b), 10, 11(a)-11(c) and 12(a)-12(c), both fluid connector 101 and electrical connector 103 are pivotally coupled to the underside of top plate 61 by corresponding mechanical linkage assemblies 104-1 and 104-2. As will be described further below, linkage assemblies 104-1 and 104-2 are used to displace connectors 101 and 103, respectively, between retracted and extended positions. It should be noted that connectors 101 and 103 are designed to matingly engage with corresponding connectors 45 and 47, respectively, on cart 17 only when disposed in their extended positions.

Figure 11A:
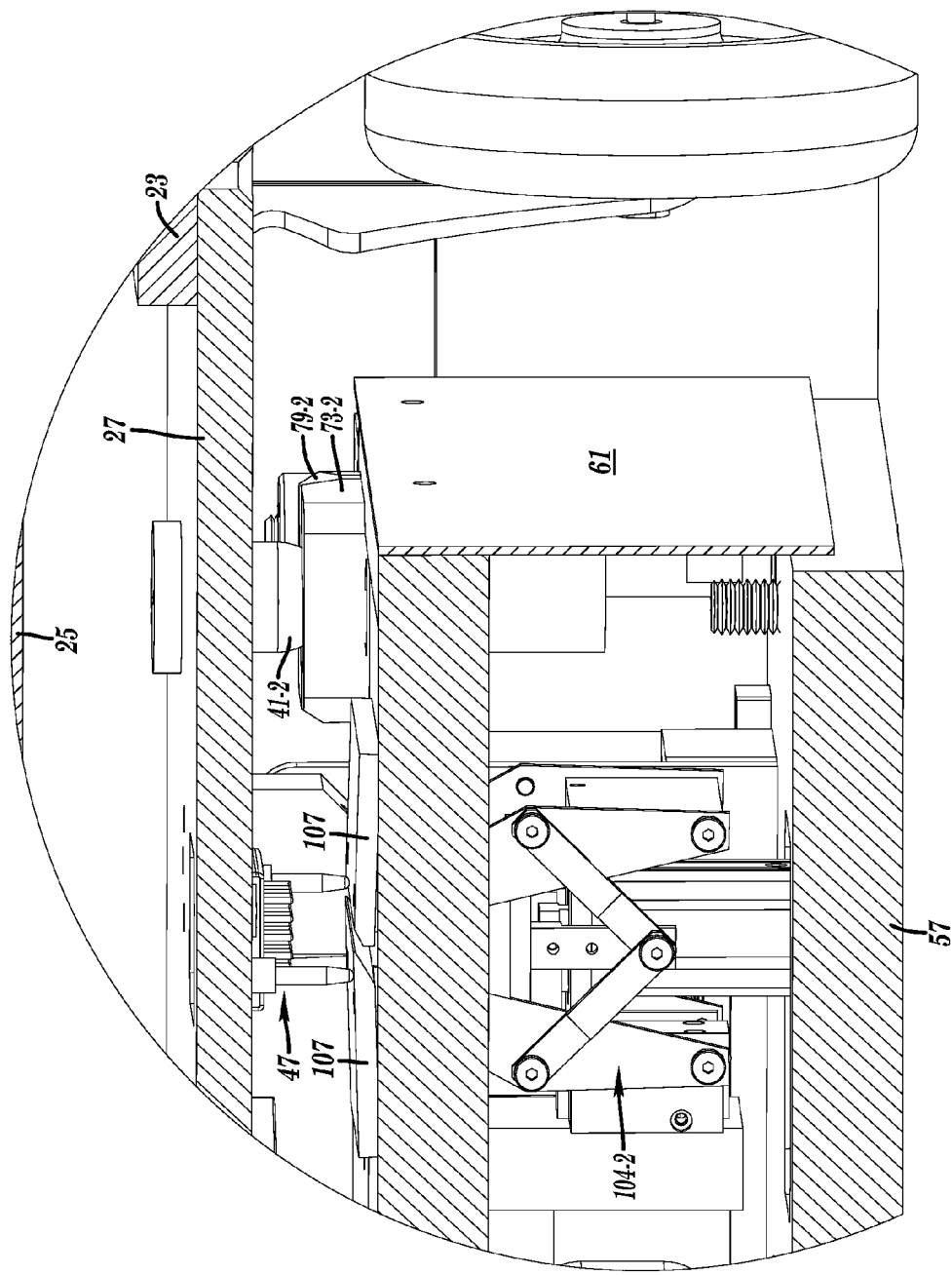
FIGS. 11(a)-(c) are fragmentary section views of the cart and docking station shown in FIG. 2(b), taken along lines 11-11, at various stages during the process of their engagement.
Figure 12A:
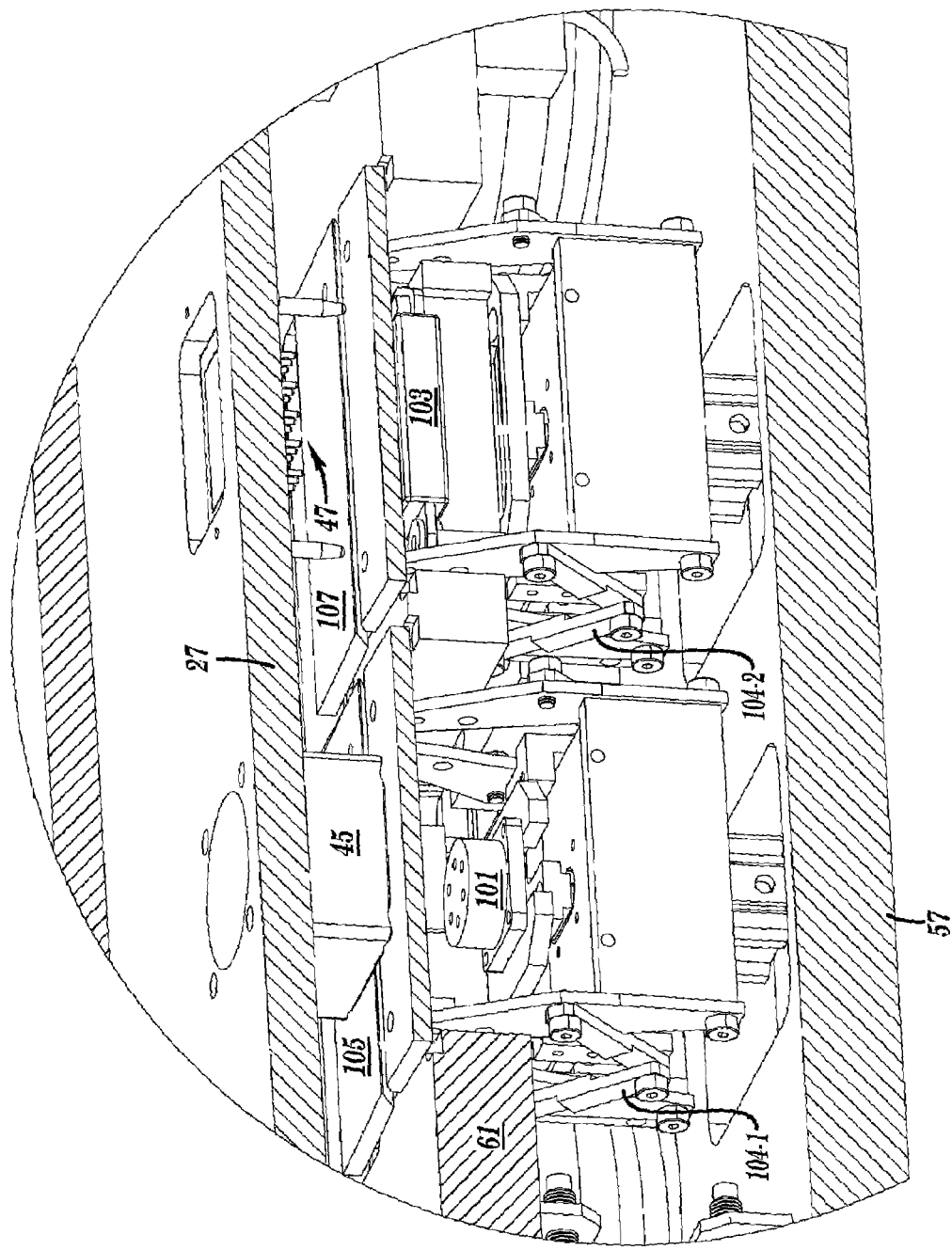
FIGS. 12(a)-(c) are fragmentary section views of the cart and docking station shown in FIG. 2(b), taken along lines 11-11, at various stages during the process of their engagement.

When disposed in their retracted positions, connectors 101 and 103 are preferably located entirely within interior cavity 59 of docking station 19 and are protected (i.e., covered) by first and second pairs of laterally extending panels 105 and 107, respectively, as seen most clearly in FIG. 7(a), FIG. 11(a) and FIG. 12(a).

Figure 10:
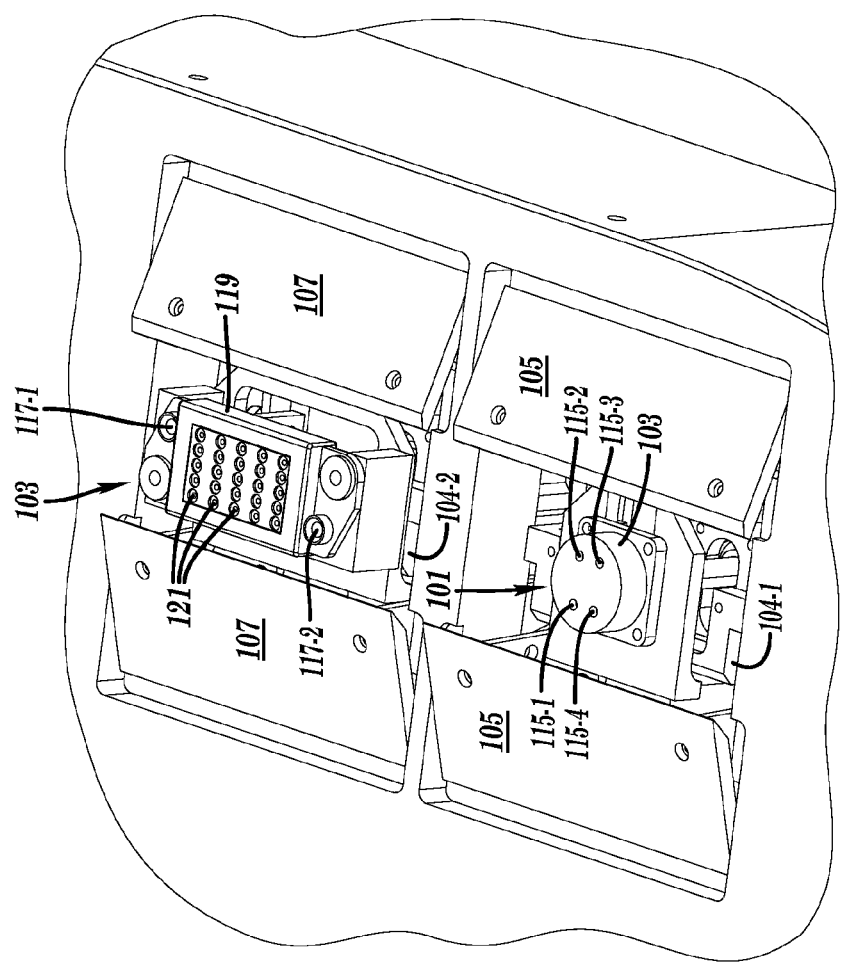
FIG. 10 is an enlarged, fragmentary, top perspective view of the docking station shown in FIG. 7(b)
Figure 11B:
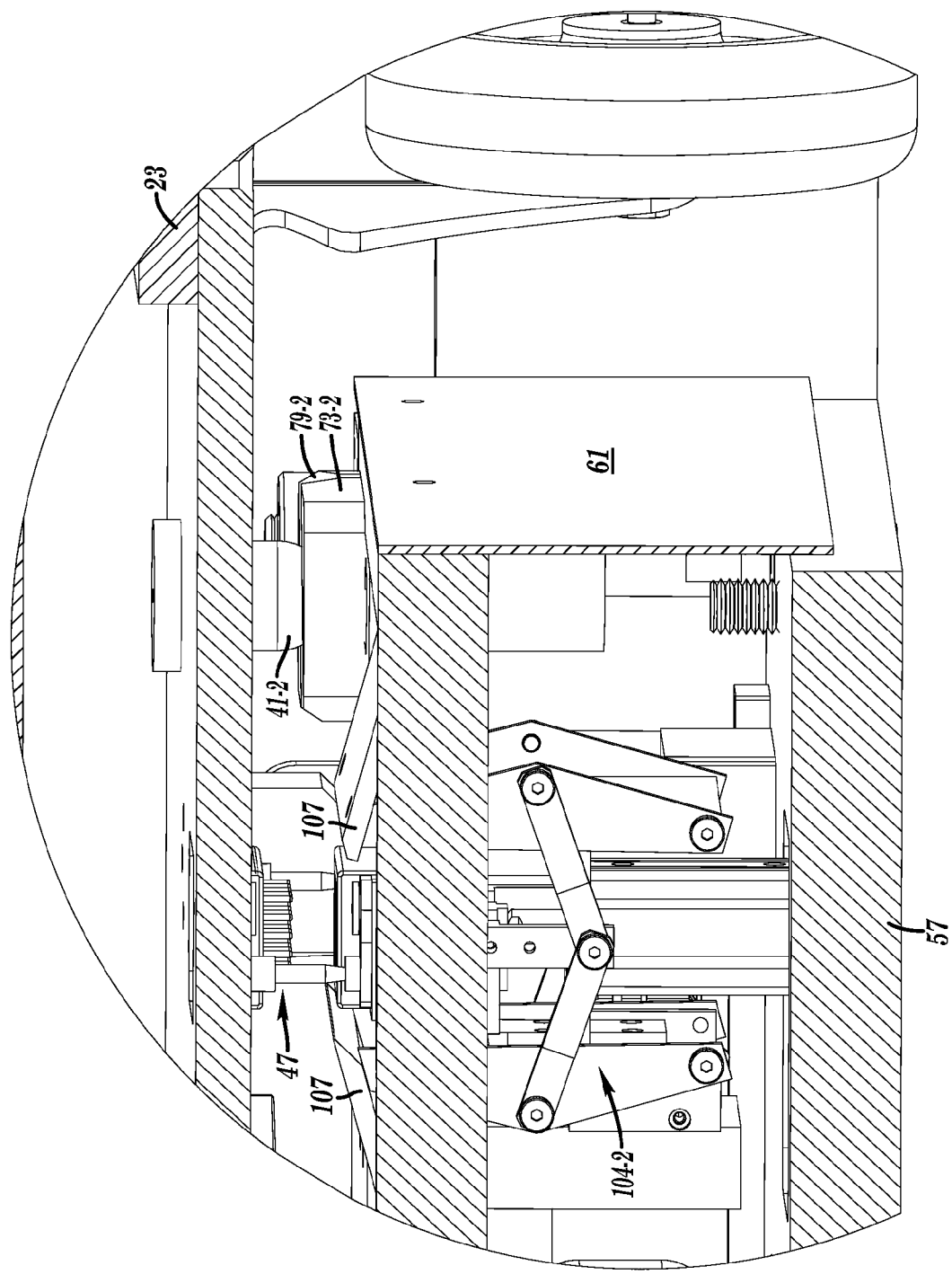
Figure 11C:
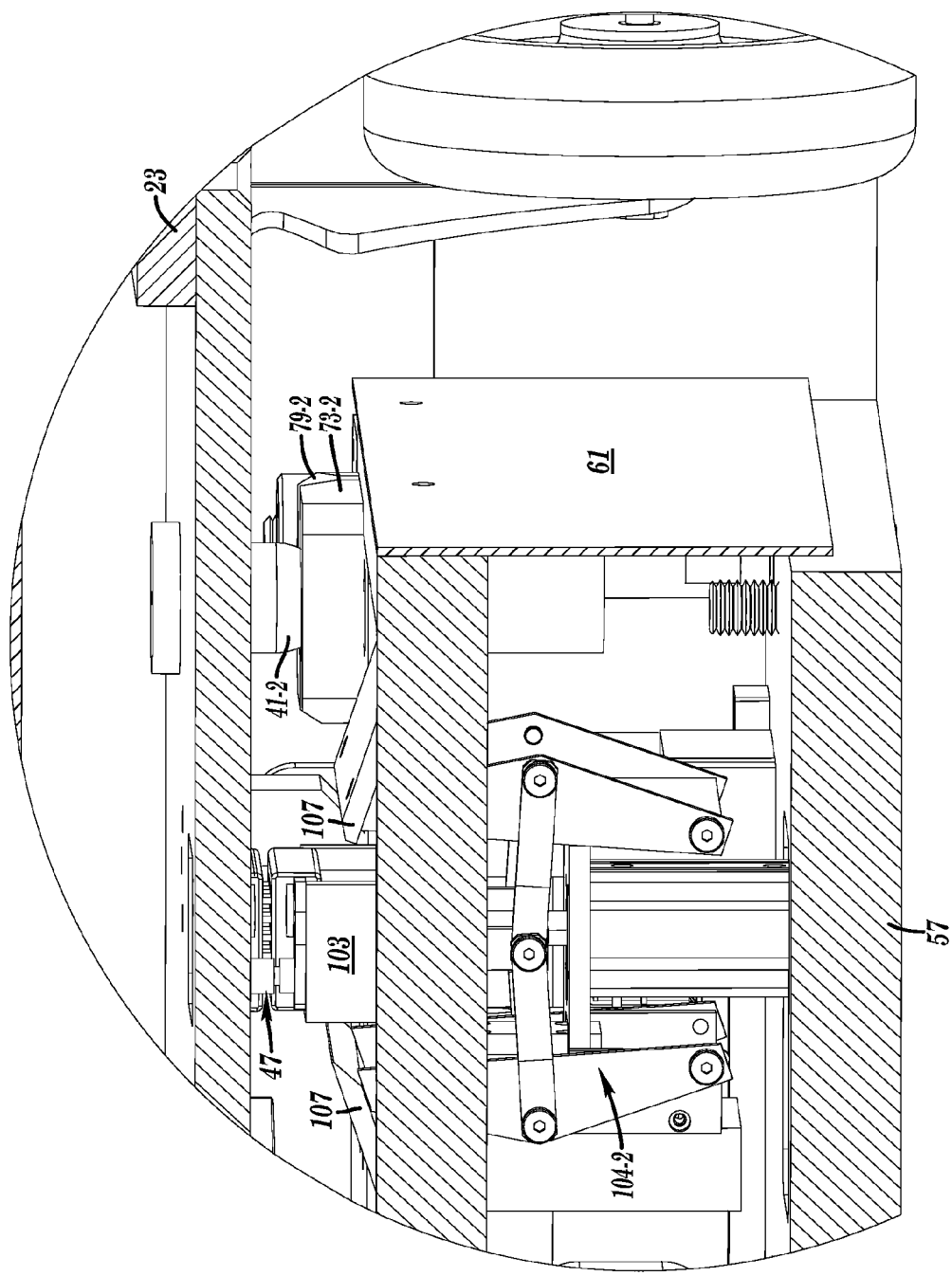
Figure 12B:
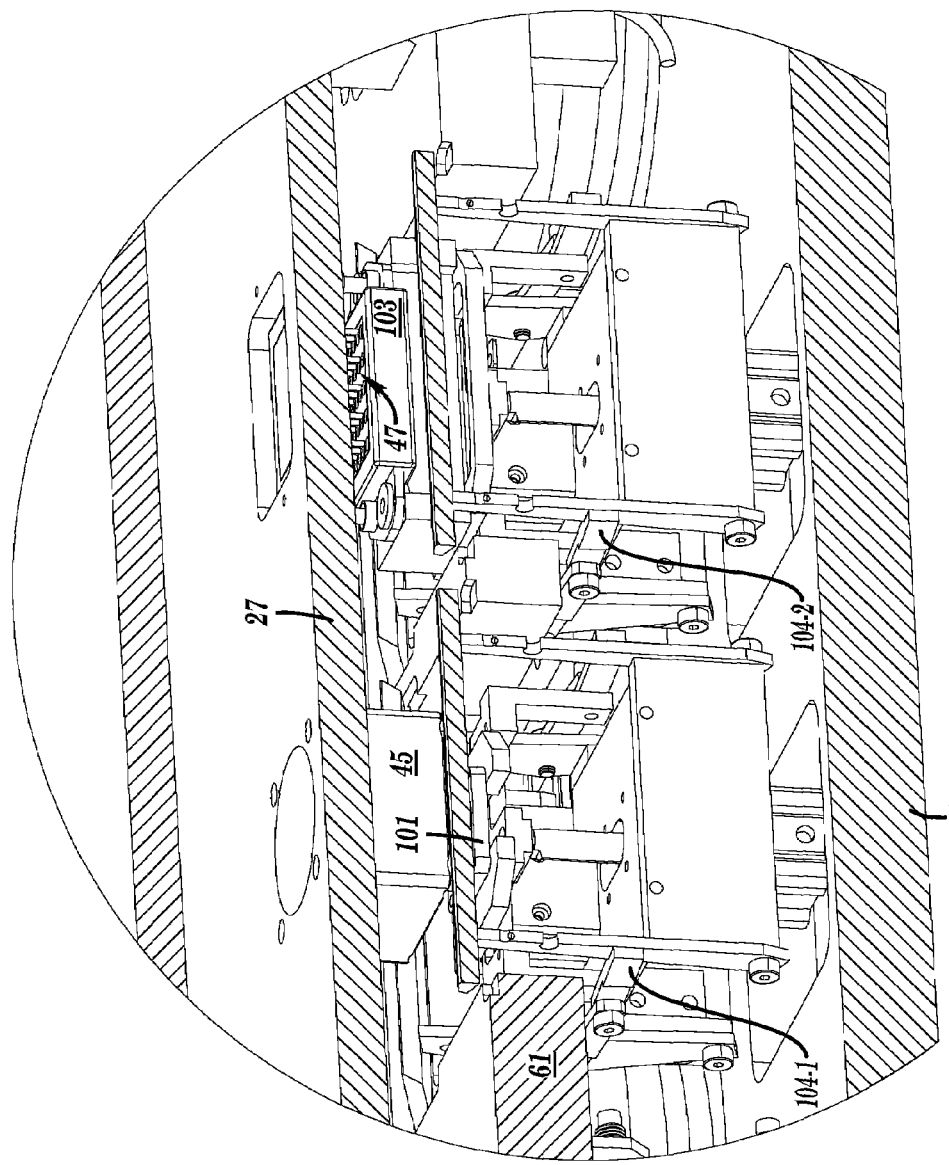
Figure 12C:
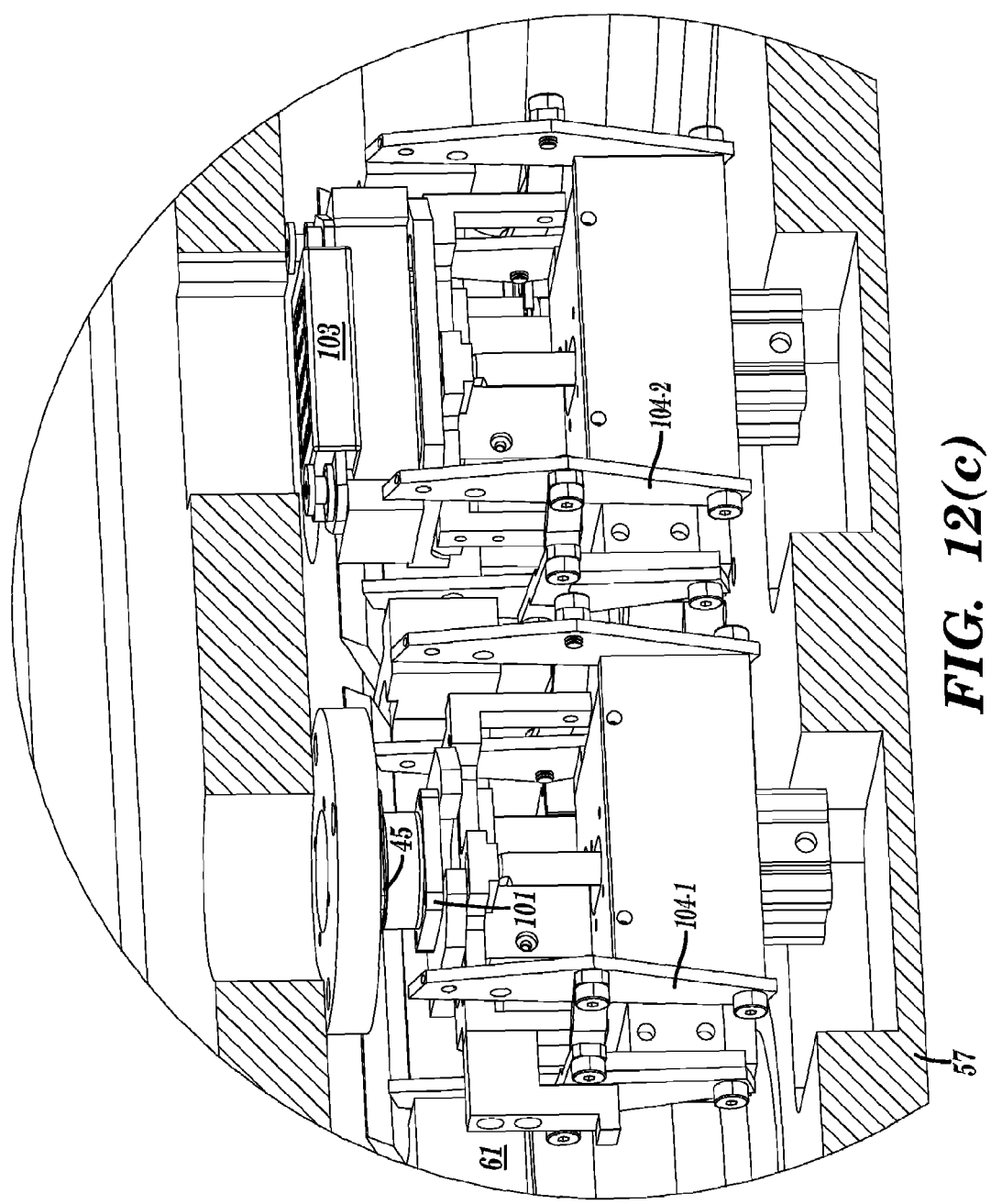

As top plate 61 rises, linkage assemblies 104-1 and 104-2 begin to pivot which, in turn, cause pairs of panels 105 and 107 to part from one another and at least partially retract within interior cavity 59, as seen most clearly in FIGS. 10, 11(b) and 12(b). With panels 105 and 107 parted as such, further rising of top plate 61 enables linkage assemblies 104-1 and 104-2 to upwardly advance connectors 101 and 103, respectively, into their extended positions above the top surface of top plate 61, as shown in FIG. 11(c) and FIG. 12(c).

As seen most clearly in FIG. 10, fluid connector 101 includes a modular cylindrical block 113 that is shaped to define four separate output fluid ports 115-1, 115-2, 115-3 and 115-4. Each output fluid port 115 is designated for fluid communication with corresponding input port 93. In addition, each output fluid port 115 is constructed to mate with a corresponding input fluid port 49 on connector 45. In this manner, the supply of a particular fluid is input into docking station 19 through a particular input port 93 formed in end plate 91, exits docking station 19 through a corresponding port 115 in connector 101 and, in turn, is input into cart 17 through an appropriate port 49 in connector 45.

Preferably, an internal valve (not shown) is located in docking station 19 between each input port 93 and its corresponding output port 115. Controlled by PLC 63, each internal valve can be used to regulate the delivery of its corresponding fluid into cart 17. For example, if a particular laboratory device 15 requires a limited number of fluid inputs, selected internal valves may be disposed in their closed positions. In this manner, docking station 19 can be readily used with a wide variety of laboratory devices 15 that have different fluid requirements, thereby rendering docking station 19 more universal in its construction, which is highly desirable.

As seen most clearly in FIG. 10, electrical connector 103 includes a pair of power contacts 117-1 and 117-2 that are electrically connected to input power connector 97 via PLC 63. Each contact 117 is adapted to electrically mate with a corresponding pin 51 on connector 47. In this manner, docking station 19 supplies power to cart 17.

Electrical connector 103 additionally includes an insulated block 119 that is designed to support a plurality of individual contacts 121, each contact 121 being electrically connected to PLC 63. It should be noted that certain sets of contacts 121 may be designated for use in conjunction with a particular operation.

As an example, certain contacts 121 may receive markers for regulating the state of the internal valve disposed in each fluid line. Specifically, if an electrical pin 53 on connector 47 connects to a designated marker contact 121, a corresponding signal is in turn sent from connector 103 to PLC 63. In response thereto, PLC 63 regulates the state of its corresponding valve in accordance therewith. In this manner, the particular configuration of pins 53 on cart connector 47 can be used to inform PLC 63 of the fluid requirements for laboratory device 15.

As another example, certain contacts 121 may be used to deliver communication signals from cart 17 to docking station 19 using any industry standard local area network (LAN) communication protocol (e.g., using an ethernet communication protocol or an RS232 communication protocol). Accordingly, communication data can be sent from laboratory device 15 to central computer system 22 via cart 17 and docking station 19, which is highly desirable.

As yet another example, certain contacts 121 may be designated as self-identification contacts. Specifically, these contacts 121 are designated to connect with certain pins 53 on cart 17 that are, in turn, electrically connected with the microprocessor embedded in cart 17. As noted above, the embedded microprocessor is preferably programmed with a unique identification code. Accordingly, the self-identification code can be sent from cart 17 to docking station 19 and, in turn, to the central computer system for testing system 11. In this manner, the central computer system is able to readily identify each laboratory device 15 that is integrated into system 11, which is highly desirable.

It should be noted that electrical connector 103 (as well as mating electrical connector 47 on cart 17) is not limited to a particular number and/or designation of contacts 121. Rather, it is to be understood that the number and/or designation of contacts 121 for electrical connector 103 could be modified for use with alternative applications without departing from the spirit of the present invention.

Process of Coupling Cart (17) to Docking Station (19)

In use, cart 17 is designed to releasably engage with any of the universal docking stations 19 in the following manner in order to seamlessly integrate a particular laboratory device 15 into automated testing system 11.

As noted above, each of the various docking stations 19 is fixedly mounted on workspace floor 21 underneath cell chamber 13. With docking stations 19 positioned as such, all of the necessary fluid input, power input and serial communication connections are made with each docking station 19. As can be appreciated, each of the aforementioned connections are intended to be permanent in nature.

In order to integrate a particular laboratory device 15 into system 11, the device 15 is first mounted on top panel 25 of cart 17, as shown in FIG. 3. As noted above, cart 17 is preferably provided with means for properly aligning device 15 on top panel 25 (e.g., complementary pins and holes) to ensure that the device 15 seamlessly integrates with the other laboratory devices in system 11.

With device 15 mounted on cart 17, the laboratory technician grasps handle 35 and manually displaces cart 17 in the forward direction towards an available docking station 19 (as represented by arrow A in FIG. 2(a)). As noted above, wheels 37 enable cart 17 to be rolled and therefore greatly facilitate in the displacement process.

As cart 17 is rolled in the direction toward the available docking station 19, posts 71-1, 71-2 and 71-3 sequentially align within the widened portion 47-1 of the channel 47 formed between tracks 39 on cart 17. Further advancement of cart 17 over docking station 19 causes posts 71 to extend within the narrowed portion 47-2 of channel 47. In this capacity, alignment posts 71 and tracks 39 together serve to roughly guide cart 17 in place above docking station 19. More specifically, posts 71 and tracks 39 reduce the likelihood of misalignment between cart 17 and docking station 19 in the lateral (i.e., side-to-side) direction.

Continued advancement of cart 17 in the forward direction eventually causes dampening blocks 43-1 and 43-2 on cart 17 to contact shock absorbers 77-1 and 77-2, respectively, on docking station 19, thereby precluding further forward displacement of cart 17. As noted above, the ability of shock absorbers 71 to decelerate cart 17 as it rolled into its proper position above docking station 19 minimizes the risk of harmful contact.

As cart 17 is being rolled into position above docking station 19, frame 23 of cart 17 actuates mechanical switch 78 on docking station 19. The actuation of mechanical switch 78 notifies PLC 63 that a cart 17 is in position above docking station 19. In response thereto, PLC 63 supplies the necessary power to bladders 67 to inflate upon activation by foot pedal 69.

With cart 17 now positioned roughly in place above the available docking station 19, the technician depresses foot pedal 69 in order to mechanically, fluidly and electrically couple cart 17 with docking station 19. The depression of foot pedal 69 generates an electrical signal that is received by PLC 63. In response thereto, PLC 63 activates the inflation of internal bladders 67. As noted above, the inflation of bladders 67 causes top plate 61 to rise relative to base 57.

As top plate 61 is displaced upward, the V-shaped groove 79 in each alignment block 73 receives a corresponding alignment pin 41 on cart 17, as seen most clearly in FIGS. 11(a)-11(c). The projection of pins 41-1, 41-2 and 41-3 into grooves 79-1, 79-2 and 79-3, respectively, results in the micro-alignment (i.e., fine-tuned, high accuracy alignment) of cart 17 relative to docking station 19.

It should be noted that, as top plate 61 continues to rise, alignment blocks 73 eventually apply an upward force to alignment pins 41. As a result, the points of contact established between alignment pins 41 and alignment blocks 73 are used to physically lift cart 17 off workspace floor 21. Top plate 61 continues upward until fixed bearings 83 abut against stops 85, thereby limiting further displacement. In this manner, docking station 19 is used to lift cart 17 a fixed, pre-determined distance off workspace floor 21, as shown in FIG. 3.

By lifting cart 17 up a pre-determined distance off workspace floor 21, cart 17 is effectively immobilized at a specified position which, in turn, disposes laboratory device 15 at a highly repeatable position. As a result, device 15 is able to more seamlessly integrate with the remainder of system 11, which is a principal object of the present invention.

Referring now to FIGS. 12(a)-12(c), the upward displacement of top plate 61 is also used to establish the necessary fluid and electrical connections between cart 17 and docking station 19. Specifically, prior to the inflation of bladders 67, top plate 61 remains in its lowered position. With top plate 61 positioned as such, connectors 101 and 103 are disposed in their retracted positions (i.e., connectors 101 and 103 are located entirely within interior cavity 59 and are covered by panels 105 and 107, respectively), as shown in FIG. 12(a). As top plate 61 begins to rise, linkage assemblies 104-1 and 104-2 retract panels 105 and 107, respectively, into interior cavity, as shown in FIG. 12(b). With panels 105 and 107 opened, fluid and electrical connectors 101 and 103 are advanced into their extended positions. Advanced in this manner, fluid and electrical connectors 101 and 103 matingly engage with corresponding fluid and electrical connectors 45 and 47, respectively, as shown in FIG. 12(c), thereby establishing fluid and electrical connection between cart 17 and docking station 19.

As can be appreciated, with cart 17 now mechanically, fluidly and electrically connected to docking station 19 in the manner described above, the laboratory device 15 mounted on cart 17 is effectively integrated into system 11 with a high level of positional accuracy, thereby ensuring seamless integration with the other laboratory devices.

In order to remove the particular device 15 from system 11, foot pedal 69 is actuated once again which, in turn, causes PLC 63 to deflate internal bladders 67. The deflation of bladders 67 lowers top plate 61 which, in turn, (i) returns wheels 37 of cart 17 back onto workspace floor 21, (ii) disconnects fluid connector 45 on cart 17 from fluid connector 101 on docking station 19 and (iii) disconnects electrical connector 47 on cart 17 from electrical connector 103 on docking station 19. At that time, cart 17 can be backed out from system 11 using handle 35.

Benefits Derived from System (11)

As detailed above, all of the necessary fluid input, power input and serial communication connections that are made with each docking station 19 are intended to be permanent in nature. Consequently, individual laboratory devices 15 can be seamlessly integrated into automated testing system 11 simply by rolling cart 17 in place above an available docking station 19 and actuating foot pedal 69. Accordingly, a plurality of individual electrical and/or fluid connections need not be made with a particular laboratory device 15 during its installation, which is in direct contrast to most conventional testing systems. As can be appreciated, the ability to readily integrate individual laboratory devices 15 into automated testing system 11 through the mating engagement between cart 17 and an associated docking station 19 provides system 11 with a number of notable advantages over prior art testing systems.

As a first advantage, the ability to quickly and easily integrate individual laboratory devices 15 into system 11 allows for both (i) the seamless integration of new, state-of-the-art devices 15 into system 11 as well as (ii) the repair and/or upgrading of existing devices 15 in system 11. As a result, the lifespan of automated testing system 11 can be substantially increased, which is a principal object of the present invention.

As a second advantage, the ability to readily withdraw a particular laboratory device 15 from automated testing system 11 and, subsequent thereto, readily re-integrate said laboratory device 15 back into automated testing system 11 enables said laboratory device 15 to be used in conjunction with multiple concurrent experiments. Due to the high costs associated the purchase with certain pieces of laboratory equipment 15, the ability to use a single laboratory device 15 in conjunction with simultaneous assays can be used to significantly reduce research costs, which is a principal object of the present invention.

As a third advantage, the process associated with the integration a particular laboratory device 15 into automated testing system 11 is significantly less time-consuming and physically demanding than the installation process associated with traditional testing systems. As a result, the present invention provides laboratory technicians with more free time to perform a greater number of assays, which is a principal object of the present invention.

Additional Applications for Carts (17) and Docking Stations (19)

It is to be understood that the use of compatible carts 17 and docking stations 19 is not limited to a cell-type (i.e., enclosed) testing environment. Rather, it is to be understood that pairs of complementary carts 17 and docking stations 19 could be implemented into alternative forms of testing environments in the life sciences industry without departing from the spirit of the present invention.

Figure 13:
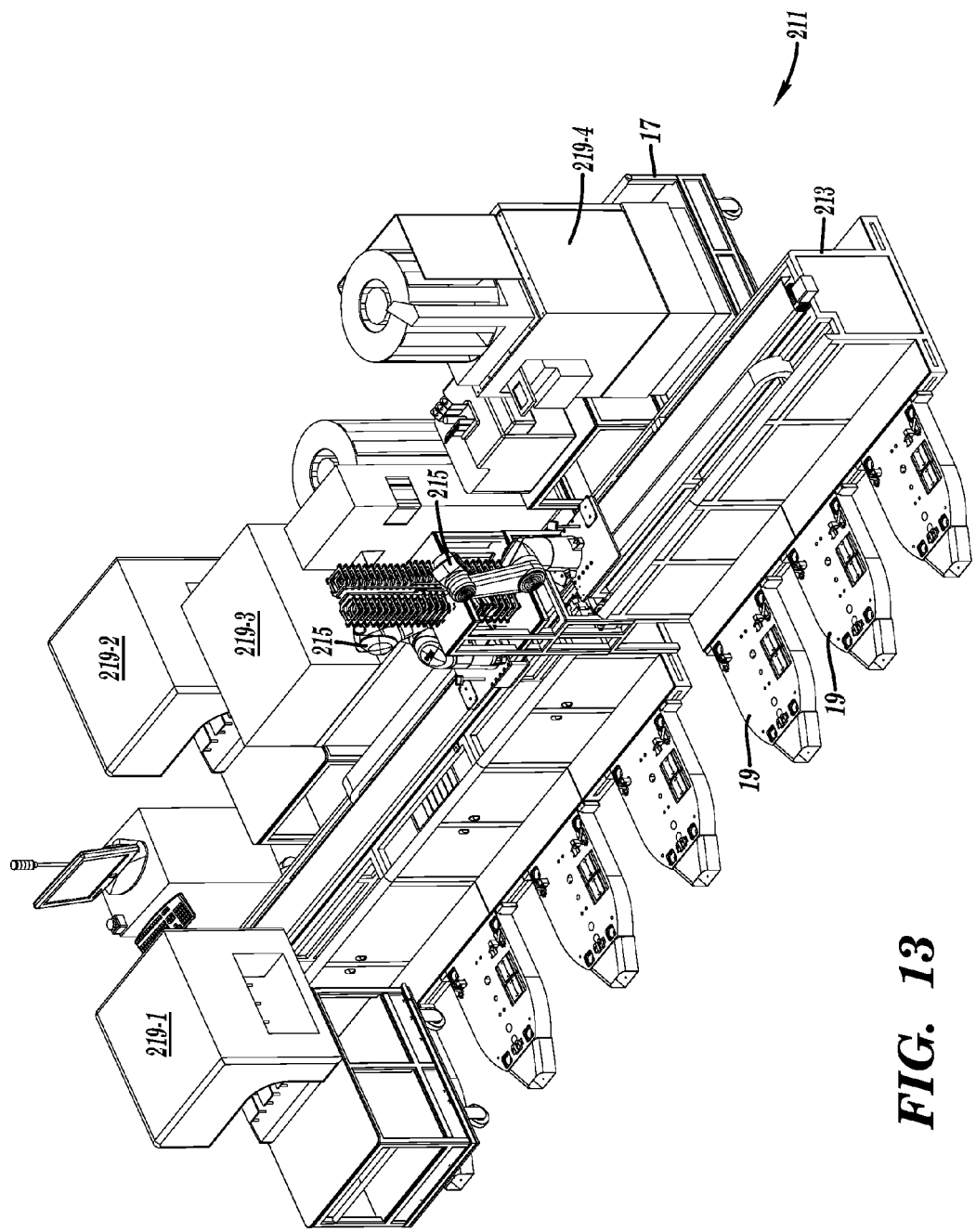
FIG. 13 is a top perspective view of an open architecture testing system constructed according to the teachings of the present invention.

For example, referring now to FIG. 13, there is shown a perspective view of an open architecture testing system that is constructed according to the teachings of the present invention, said testing system being identified generally by reference numeral 211. As can be seen, system 211 comprises an elongated, linear track 213 (rather than the flat table surface 13 provided in system 11). A pair of multi-axis robotic arms 215 are mounted on track 213 and are preferably capable of being slidably displaced along its longitudinal axis.

In system 211, a series of docking stations 19 are linearly arranged both in front of and behind track 213, each docking station 19 being fixedly mounted in place on the workspace flooring. In the same manner as described above in conjunction with system 11, each docking station 19 in system 211 is adapted to matingly receive a corresponding cart 17. As a result, various types of laboratory devices (some of which are identified generally in FIG. 13 as devices 219-1 through 219-4) that are mounted on carts 17 can be readily integrated into system 211.

It should be noted that, by flanking both sides of the linear track 213 with docking stations 19, the number of laboratory devices 219 that can be integrated into system 21 is maximized, thereby rendering system 211 compact in size but highly functional in its capabilities, which is highly desirable.

The versions of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A system comprising:
 a frame comprising:
  a plurality of wheels coupled thereto for supporting the frame on a surface, the frame configured to have a laboratory device for performing a particular function mounted thereto, and
  a first connector on a bottom of the frame, the first connector operationally coupled to the laboratory device;
 a fixedly mounted docking station including:
  a base,
  a top plate slidably mounted over the base,
  a second connector extendable from the top plate, and
  means for moving the top plate relative to the base to: a) engage the top plate with a bottom of the frame such that the plurality of wheels disengage the surface, and
  b) establish at least one of a fluid connection or an electrical connection between the first connector and the second connector.

2. The system of claim 1, wherein the second connector is movable between a retracted position in which the second connector is covered by a movable cover and an extended position in which the second connector is exposed by the movable cover.

3. The system of claim 1, wherein, with the top plate engaged with the frame, both fluid and electrical connections are established between the laboratory device and the docking station.

4. The system of claim 1, wherein the docking station comprises:
 (a) at least one fluid input port, each port being designated to receive the delivery of a particular fluid into the docking station,
 (b) an input power connector for receiving the supply of power to the docking station, and
 (c) at least one communication signal connector for transmitting communication signals to and from the docking station.

5. The system of claim 1, wherein the first connector on the frame includes a plurality of individual input fluid ports, each port being designated to deliver a particular fluid to the laboratory device.

6. The system of claim 5, wherein the second connector on the docking station includes a plurality of individual output fluid ports, each output fluid port being designated to deliver a particular fluid to a corresponding input fluid port in the first connector.

7. The system of claim 1, wherein the first connector comprises an electrical connector that is electrically connected to the laboratory device.

8. The system of claim 1, wherein the frame further comprises:
 (a) a top panel secured to the top of the frame, the top panel configured to support the laboratory device, and
 (b) a bottom panel secured to the underside of the frame.

9. The system of claim 8, wherein the frame further comprises:
 (a) an alignment pin fixedly coupled to the bottom panel, and
 (b) a pair of symmetrical, spaced apart tracks fixedly coupled to the bottom panel.

10. The system of claim 9, wherein the docking station further comprises:
 (a) an alignment block fixedly coupled to the top plate, the alignment block being shaped to define a groove;
 (b) an alignment post fixedly coupled to the base and at least partially protruding out through an opening in the top plate; and
 (c) a stop assembly fixedly coupled to the base, the stop assembly limiting the degree of displacement of the top plate relative to the base.

11. The system of claim 10, wherein, with the top plate engaged with the frame, the groove in the alignment block on the docking station fittingly receives the alignment pin on the frame to ensure accurate positioning between the docking station and the frame.

12. The system of claim 11, wherein the tracks on the frame define a channel configured to receive the alignment post on the docking station in order to generally align the fame in position above the docking station prior to engagement.

* * * * *